(12) United States Patent
Thomas et al.

(10) Patent No.: US 7,283,864 B2
(45) Date of Patent: Oct. 16, 2007

(54) METHOD AND APPARATUS FOR IDENTIFYING PATIENTS WITH WIDE QRS COMPLEXES

(75) Inventors: Brian P. Thomas, Blaine, MN (US); Jay Millerhagen, Lino Lakes, MN (US); Michael Gebauer, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 161 days.

(21) Appl. No.: 11/055,731

(22) Filed: Feb. 10, 2005

(65) Prior Publication Data
US 2006/0178707 A1   Aug. 10, 2006

(51) Int. Cl.
*A61B 5/04*   (2006.01)
(52) U.S. Cl. ......................... 600/516; 607/30
(58) Field of Classification Search ................ 600/516; 607/9, 25, 30
See application file for complete search history.

(56) References Cited

U.S. PATENT DOCUMENTS

| | | | |
|---|---|---|---|
| 3,768,487 A | 10/1973 | Rose | |
| 4,313,443 A * | 2/1982 | Frosch et al. ............... | 600/377 |
| 4,458,691 A | 7/1984 | Netravali | |
| 5,469,858 A | 11/1995 | Osborne | |
| 5,544,661 A | 8/1996 | Davis et al. | |
| 5,634,469 A | 6/1997 | Bruder et al. | |
| 5,694,942 A | 12/1997 | Escalona | |
| 5,740,808 A | 4/1998 | Panescu et al. | |
| 5,827,196 A | 10/1998 | Yeo et al. | |
| 6,115,630 A | 9/2000 | Stadler et al. | |
| 6,144,880 A | 11/2000 | Ding et al. | |
| 6,267,778 B1 * | 7/2001 | Cohen ......................... | 607/9 |
| 6,491,639 B1 | 12/2002 | Turcott | |
| 6,597,951 B2 * | 7/2003 | Kramer et al. ................. | 607/9 |
| 6,622,040 B2 | 9/2003 | Ding et al. | |
| 6,705,999 B2 | 3/2004 | Yu et al. | |
| 6,751,504 B2 | 6/2004 | Fishler | |
| 6,766,189 B2 | 7/2004 | Yu et al. | |
| 6,804,555 B2 | 10/2004 | Warkentin | |
| 6,993,389 B2 | 1/2006 | Ding et al. | |
| 2004/0116975 A1 | 6/2004 | Yu et al. | |
| 2004/0162496 A1 | 8/2004 | Yu et al. | |
| 2005/0197674 A1 | 9/2005 | McCabe et al. | |
| 2005/0216065 A1 | 9/2005 | Ding et al. | |

* cited by examiner

*Primary Examiner*—Carl H. Layno
*Assistant Examiner*—Natasha Patel
(74) *Attorney, Agent, or Firm*—Schwegman, Lundberg, & Woessner, P.A.

(57) ABSTRACT

A medical device programmer or other external system capable of programming an implantable CRM device includes a wide-QRS detection and alerting system. Upon detection of a wide QRS complex, a wide-QRS indicator produces a visual indication of the detection using one or more presentation devices such as a display screen and a printer to alert a physician or other caregiver.

35 Claims, 6 Drawing Sheets

METHOD AND APPARATUS FOR IDENTIFYING PATIENTS WITH WIDE QRS COMPLEXES

TECHNICAL FIELD

This document generally relates to cardiac rhythm management (CRM) systems and particularly, but not by way of limitation, to such a system that identifies patients with wide QRS complexes.

BACKGROUND

The heart is the center of a person's circulatory system. The left portions of the heart, including the left atrium (LA) and left ventricle (LV), draw oxygenated blood from the lungs and pump it to the organs of the body to provide the organs with their metabolic needs for oxygen. The right portions of the heart, including the right atrium (RA) and right ventricle (RV), draw deoxygenated blood from the body organs and pump it to the lungs where the blood gets oxygenated. These mechanical pumping functions are accomplished by contractions of the heart. In a normal heart, the sinoatrial (SA) node, the heart's natural pacemaker, generates electrical impulses, called action potentials, that propagate through an electrical conduction system to various regions of the heart to cause the muscular tissues of these regions to depolarize and contract at a normal sinus rate.

Electrocardiography (ECG) is known to indicate the functions of the electrical conduction system by monitoring the action potentials at various portions of the heart. A QRS complex is a segment of an ECG signal that indicates depolarization of the ventricles. An abnormally wide QRS complex is an indication that the conduction of the electrical impulses through the ventricles is prolonged. The prolonged conduction may result from conditions related to heart failure, including hypertrophy or dilatation of one or both ventricles and/or blockage of the Purkinje fibers that conduct the electrical impulses in the ventricles. Thus, physicians and other caregivers use the width of the QRS complex as an indication of abnormal cardiac conditions, including heart failure, that may need medical treatments.

Implantable CRM devices such as pacemakers and defibrillators are used to treat cardiac arrhythmias, heart failure, and other cardiovascular disorders by delivering electrical energy to the heart. An abnormally wide QRS complex is one of the factors that prompt a physician or other caregiver to consider an application or adjustment of a cardiac electrical therapy using an implantable CRM device.

For these and other reasons, there is a need for an easy and convenient way to detect wide QRS complexes and, if detected, communicate the result to a physician or other caregiver for consideration of applying or adjusting the cardiac electrical therapy.

SUMMARY

A medical device programmer or other external system capable of programming an implantable CRM device includes a wide-QRS detection and alerting system. Upon detection of a wide QRS complex, a wide-QRS indicator produces a visual indication of the detection using one or more presentation devices such as a display screen and a printer to alert a physician or other caregiver.

In one embodiment, a CRM system includes an implantable medical device and an external system communicatively coupled to the implantable medical device via telemetry. The implantable medical device includes a pacing circuit to deliver pacing pulses and an implant controller to control the delivery of the pacing pulses. The external system includes a user interface, a programming circuit, and a wide-QRS detection and alerting circuit. The user interface includes one or more user input devices and one or more presentation devices. The programming circuit allows for programming of the implantable medical device. The wide-QRS detection and alerting circuit includes a wide-QRS detector and a wide-QRS indicator. The wide-QRS detector receives an ECG signal and detects a wide QRS complex from the ECG signal. The wide-QRS indicator produces a wide-QRS indication using the one or more presentation devices when the wide QRS complex is detected.

In one embodiment, a medical device programmer includes an external telemetry circuit, a user interface, a programming circuit, a surface ECG sensing circuit, and a wide-QRS detection and alerting circuit. The external telemetry circuit allows the medical device programmer to communicate with an implantable medical device. The user interface includes one or more user input devices and one or more presentation devices. The programming circuit allows for the programming of the implantable medical device. The surface ECG sensing circuit senses at least one surface ECG signal. The wide-QRS detection and alerting circuit includes a wide-QRS detector and a wide-QRS indicator. The wide-QRS detector receives the surface ECG signal and detects a wide QRS complex from the surface ECG signal. The wide-QRS indicator produces a wide-QRS indication using the one or more presentation devices when the wide QRS complex is detected.

In one embodiment, an external system communicates with an implantable medical device coupled to implantable electrodes. The external system includes an external telemetry circuit, a programming circuit, a user interface, and a wide-QRS detection and alerting circuit. The external telemetry circuit receives at least one wireless ECG signal from the implantable medical device. The wireless ECG signal is a signal sensed through the implantable electrodes and approximating a surface ECG signal. The programming circuit allows for programming of the implantable medical device. The user interface includes one or more presentation devices. The wide-QRS detection and alerting circuit includes a wide-QRS detector and a wide-QRS indicator. The wide-QRS detector receives the wireless ECG signal and detects a wide QRS complex from the wireless ECG signal. The wide-QRS indicator produces a wide-QRS indication using the one or more presentation devices when the wide QRS complex is detected.

In one embodiment, a method is provided for operating a medical device programmer communicating with an implantable medical device. A surface ECG signal is sensed by using a surface ECG sensing circuit of the medical device programmer. A QRS width is measured from the surface ECG signal. A wide QRS complex is detected by comparing the measured QRS width to a predetermined threshold QRS width. When the QRS width exceeds the predetermined threshold QRS width, a visual indication of a detection of the wide QRS complex is presented using a presentation device of the medical device programmer.

In one embodiment, a method is provided for operating an external system communicating with an implantable medical device coupled to implantable electrodes. A wireless ECG signal is received from the implantable medical device. The wireless ECG is a signal sensed through the implantable electrodes and approximating a surface ECG. A QRS width is measured from the wireless ECG signal. A wide QRS complex is detected by comparing the QRS width to a predetermined threshold QRS width. When the QRS width exceeds the predetermined threshold QRS width, a visual indication of a detection of the wide QRS complex is presented using a presentation device of the external system.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

In the drawings, which are for illustrative purposes only and not necessarily drawn to scale, like numerals describe similar components throughout the several views. The drawings illustrate generally, by way of example, but not by way of limitation, various embodiments discussed in the present document.

DETAILED DESCRIPTION

In the following detailed description, reference is made to the accompanying drawings that form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their equivalents.

It should be noted that references to "an", "one", or "various" embodiments in this document are not necessarily to the same embodiment, and such references contemplate more than one embodiment. In this document, "electrogram" or "intracardiac electrogram" refers to a cardiac electrical signal sensed with one or more implantable sensing electrodes placed in or on the heart. "Surface ECG" refers to a cardiac electrical signal sensed with electrodes attached onto the exterior surface of the skin. "Wireless ECG" refers to a signal approximating the surface ECG, acquired without using surface (non-implantable, skin contact) electrodes. "Subcutaneous ECG" is a form of wireless ECG and includes a cardiac electrical signal sensed through electrodes implanted in subcutaneous tissue, such as through electrodes incorporated onto an implantable medical device that is subcutaneously implanted. A surface ECG is morphologically different from an intracardiac electrogram because of the difference in the sources that produce these signals. As reflected in their corresponding morphologies, the surface ECG results from electrical activities of the entire heart, while the intracardiac electrogram primarily results from the spread of electrical activity in a region in close proximity to the one or more implantable sensing electrodes placed in or on the heart. The wireless ECG, including but not being limited to the subcutaneous ECG, has a morphology that approximates that of the surface ECG and reflects electrical activities of a substantial portion of the heart, up to the entire heart.

This document discusses, among other things, a CRM system that automatically identifies patients with wide QRS complexes. A wide QRS complex is a QRS complex having a width that exceeds a threshold QRS width. The CRM system includes an implantable medical device and a medical device programmer or other external system communicating with the implantable medical device. When a wide QRS complex is detected, the medical device programmer or other external system provides a physician or other caregiver with a conspicuous visual indication using one or more presentation devices such as a display screen and a printer.

Figure 1:
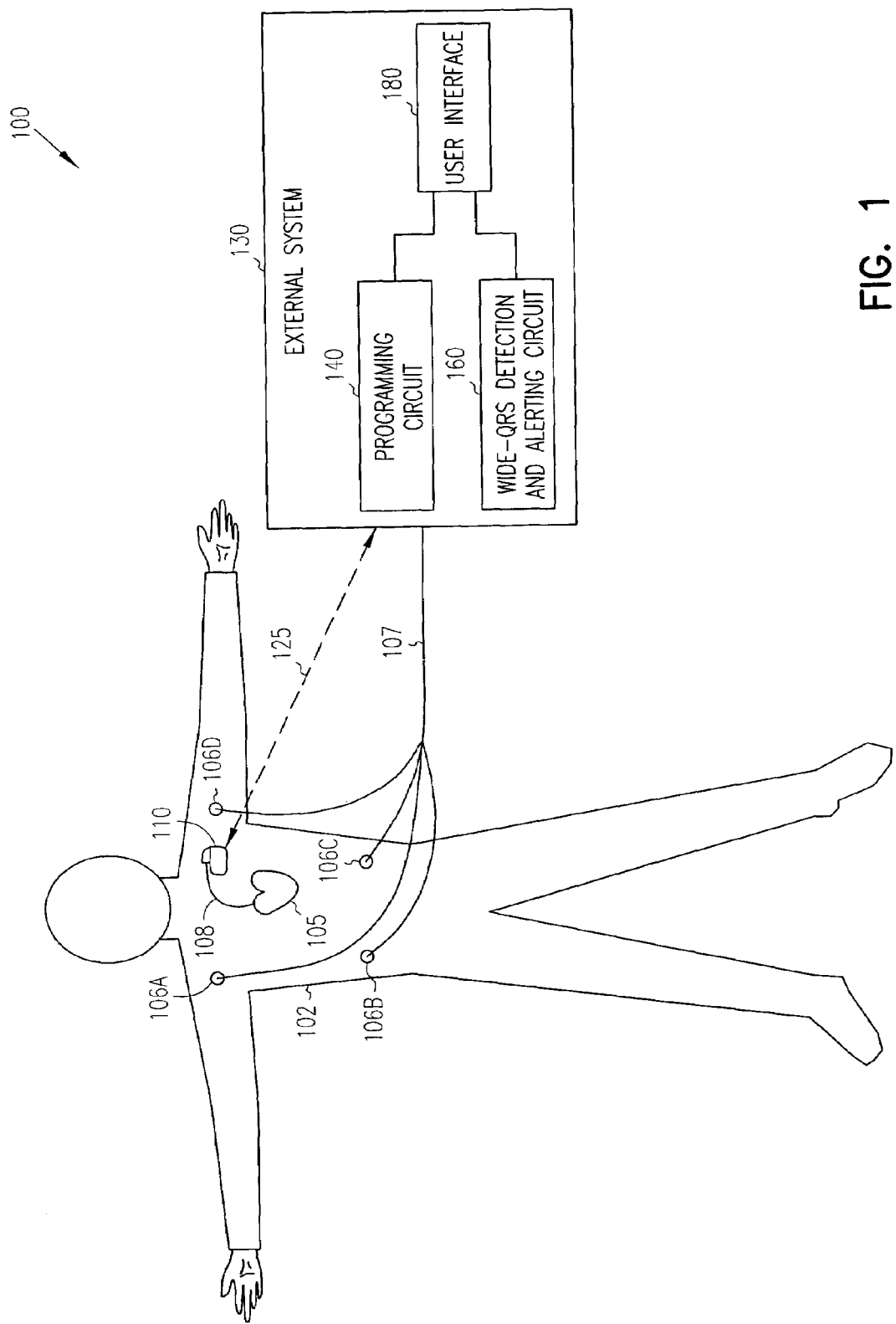
FIG. 1 is an illustration of an embodiment of a CRM system and portions of an environment in which the CRM system is used.

FIG. 1 is an illustration of one embodiment of a CRM system 100 and portions of the environment in which CRM system 100 is used. System 100 includes an implantable medical device 110, a lead system 108, an external system 130, a wireless telemetry link 125, surface ECG electrodes 106A-D, and an ECG lead cable 107.

After implantation, implantable medical device 110 operates within a body 102 to sense activities of a heart 105 and deliver one or more therapies to heart 105. Implantable medical device 110 includes, but is not limited to, one or more of a pacemaker, a cardioverter/defibrillator, a cardiac resynchronization therapy (CRT) device, a cardiac remodeling control therapy (RCT) device, a drug delivery device, and a biological therapy device.

Lead system 108 provides one or more electrical and/or other connections between implantable medical device 110 and heart 105. In one embodiment, lead system 108 includes one or more pacing and/or defibrillation leads each having one or more electrodes for sensing cardiac electrical signals and/or delivering electrical pulses to heart 105. In one embodiment, one or more intracardiac sensors are incorporated into lead system 108 to sense signals such as heart sounds, intracardiac pressures, and chemical parameters of the blood.

In one embodiment, implantable medical device 110 is capable of sensing one or more wireless ECG signals and transmitting them to external device 130. The one or more wireless ECG signals are sensed using electrodes incorporated into lead system 108 and/or electrodes incorporated onto implantable medical device 110. In one specific embodiment, the one or more wireless ECG signals include one or more subcutaneous ECG signals sensed through implantable subcutaneous electrodes.

External system 130 communicates with implantable medical device 110 through telemetry link 125. External system 130 allows a physician or other caregiver to communicate with implantable medical device 110. External system 130 includes a programming circuit 140, a wide-QRS detection and alerting circuit 160, and a user-interface 180. Programming circuit 140 allows the physician or other caregiver to program implantable medical device 110. Wide-QRS detection and alerting circuit 160 detects a wide QRS complex, i.e., a QRS complex having a width or duration that is longer than a predetermined threshold, from an ECG signal indicative of cardiac electrical activities of heart 105 and produces a visual indication of each detection of a wide QRS complex for presentation on user interface 180. In one embodiment, the ECG signal is a wireless ECG signal sensed by implantable medical device 110. In another embodiment, the ECG signal is sensed through surface electrodes 106A-D, which are connected to external system 130 through an ECG lead cable 107.

In one embodiment, external system 130 includes an external medical device programmer. The medical device programmer includes programming circuit 140, the wide-QRS detection and alerting circuit 160, and user interface 180. In another embodiment, external system 130 is a patient management system including an external device, a telecommunication network, and a remote device. The external device is placed within the vicinity of implantable medical device 110 and communicates with implantable medical device 110 bi-directionally via telemetry link 125. The remote device is in a remote location and communicates with the external device bi-directionally through the telecommunication network, thus allowing a physician or other caregiver to monitor and treat a patient from a distant location. In one embodiment, the remote device includes at least portions of programming circuit 140, the wide-QRS detection and alerting circuit 160, and user interface 180.

Telemetry link 125 provides for communication between implantable medical device 110 and external system 130. In one embodiment, telemetry link 125 is an inductive telemetry link. In an alternative embodiment, telemetry link 125 is a far-field radio-frequency telemetry link. Telemetry link 125 provides for data transmission from implantable medical device 110 to external system 130. This may include, for example, transmitting information indicative of the device type of implantable medical device 110, transmitting data indicative of the current operational mode(s) and parameter values, transmitting real-time physiological data acquired by implantable medical device 110, extracting physiological data acquired by and stored in implantable medical device 110, extracting therapy history data, and extracting data indicating an operational status (e.g., battery status and lead impedance). Telemetry link 125 also provides for data transmission from external system 130 to implantable medical device 110. This may include, for example, parameters for programming implantable medical device 110 to acquire physiological data, to perform at least one self-diagnostic test (such as for a battery status and lead impedance status), and/or to deliver at least one therapy. The physiological data represent signals acquired by implantable medical device 110. The signals include, but are not limited to, one or more of electrograms, wireless ECG signals, heart sounds or signals indicative of heart sounds, activity level signals, impedance signals, pressure or pressure-indicating signals, and respiratory signals. In one embodiment, the physiological data also include parameters measured from one or more of these signals. In one embodiment, external system 130 or the physician or other caregiver determines parameter values for programming implantable medical device 110 based on these physiological data.

Figure 2:
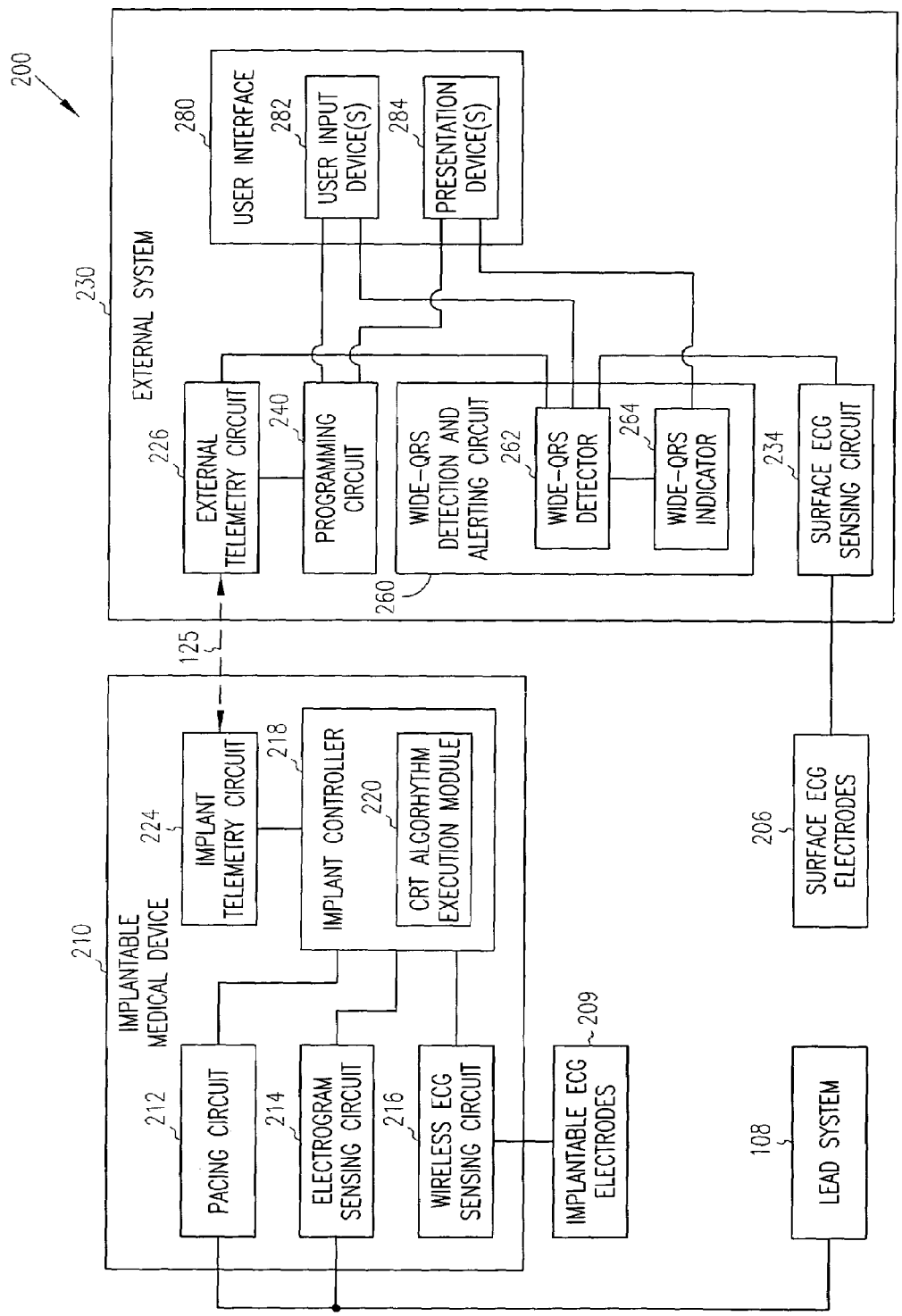
FIG. 2 is a block diagram illustrating an embodiment of a circuit of the CRM system.

FIG. 2 is a block diagram illustrating an embodiment of a circuit of a CRM system 200. CRM system 200 represents one embodiment of CRM system 100 and includes an implantable medical device 210 coupled to implantable ECG electrodes 209 and lead system 108, an external system 230 coupled to surface ECG electrodes 206, and wireless telemetry link 125. As illustrate in FIG. 2, CRM system 200 is capable of detecting wide QRS complexes from either a wireless ECG signal sensed by implantable medical device 210 through implantable ECG electrodes 209 or a surface ECG signal sensed by external system 230 through surface ECG electrodes 206. In various specific embodiments, CRM system 200 detects wide QRS complexes from the wireless ECG signal, the surface ECG signal, or both.

Implantable medical device 210 is a specific embodiment of implantable medical device 110 and includes a pacing circuit 212, an electrogram sensing circuit 214, a wireless ECG sensing circuit 216, an implant controller 218, and an implant telemetry circuit 224. Pacing circuit 212 delivers pacing pulses to the heart. In one embodiment, implantable medical device 210 includes one or more additional therapy delivery devices such as a cardioversion/defibrillation circuit to deliver cardioversion/defibrillation pulses, a substance delivery device to deliver chemical and/or biological agents, and a biological therapy device to deliver signals controlling a gene therapy. Electrogram sensing circuit 214 senses one or more electrograms. Wireless ECG sensing circuit 216 senses one or more wireless ECG signals through implantable ECG electrodes 209. Implantable ECG electrodes 209 include intracardiac electrodes, epicardial electrodes, subcutaneous electrodes, or any combination of such electrodes. In one embodiment, implantable ECG electrodes 209 include subcutaneous electrodes that are incorporated onto implantable medical device 210. Examples of a circuit and implantable electrodes for sensing the wireless ECG is discussed in U.S. patent application Ser. No. 10/795,126, entitled "WIRELESS ECG IN IMPLANTABLE DEVICES," filed on Mar. 5, 2004, assigned to Cardiac Pacemakers, Inc., which is incorporated herein by reference in its entirety. Implant controller 218 controls the sensing of the electrograms and wireless ECG signals and the delivery of pacing pulses and/or other therapies. In one embodiment, implantable controller 218 includes a CRT algorithm execution module 220 that controls the delivery of pacing pulses by executing a CRT algorithm. The CRT pacing algorithm is executed with one or more pacing parameters approximately optimized to maximize a measure of hemodynamic performance. Implant telemetry circuit 224 provides implantable medical device 210 with the telemetry capability required for communicating with external device 230 via telemetry link 125.

External system 230 is a specific embodiment of external system 130 and includes an external telemetry circuit 226, a programming circuit 240, a surface ECG sensing circuit 234, a wide-QRS detection and alerting circuit 260, and a user interface 280. External telemetry circuit 226 provides external system 230 with the telemetry capability required for communicating with implantable medical device 210 via telemetry link 125. Programming circuit 240 programs implantable medical device 210 by producing programming instructions based on user input received through user interface 280. External telemetry circuit 226 receives these programming instructions and transmits them to implantable medical device 210. In one embodiment, external telemetry circuit 226 receives one or more wireless ECG signals from implantable medical device 210. Surface ECG sensing circuit 234 senses one or more surface ECG signals using surface ECG electrodes 206. Wide-QRS detection and alerting circuit 260 includes a wide QRS detector 262 and a wide-QRS indicator 264. Wide QRS detector 262 receives an ECG signal and detects wide QRS complexes from the ECG signal. In one embodiment, the ECG signal is a surface ECG signal received from surface ECG sensing circuit 234. In another embodiment, the ECG signal is a wireless ECG signal received from external telemetry circuit 226, which receives that wireless ECG signal from implantable medical device 210. Wide QRS detector 262 detects the wide QRS complexes by detecting QRS complexes, measuring the width of each QRS complex, and comparing the width to a predetermined threshold QRS width. When a wide QRS complex is detected, wide-QRS indicator 264 produces a wide-QRS indication for presentation using user interface 280. Additional details of wide-QRS detection and alerting circuit 260 are discussed below with reference to FIG. 4. User interface 280 includes one or more user input devices 282 and one or more presentation devices 284. User input device(s) 282 allow the physician or other caregiver to control the operation of implantable medical device 210, and to control the operation of external system 230 including wide-QRS detection and alerting circuit 260. Presentation device(s) 282 displays and/or prints information related to the patient's physiological activities and conditions, including the wide-QRS indication and information related to the operation of implantable medical device 210. Additional details of user interface 280 are discussed below with reference to FIG. 3.

Figure 3:
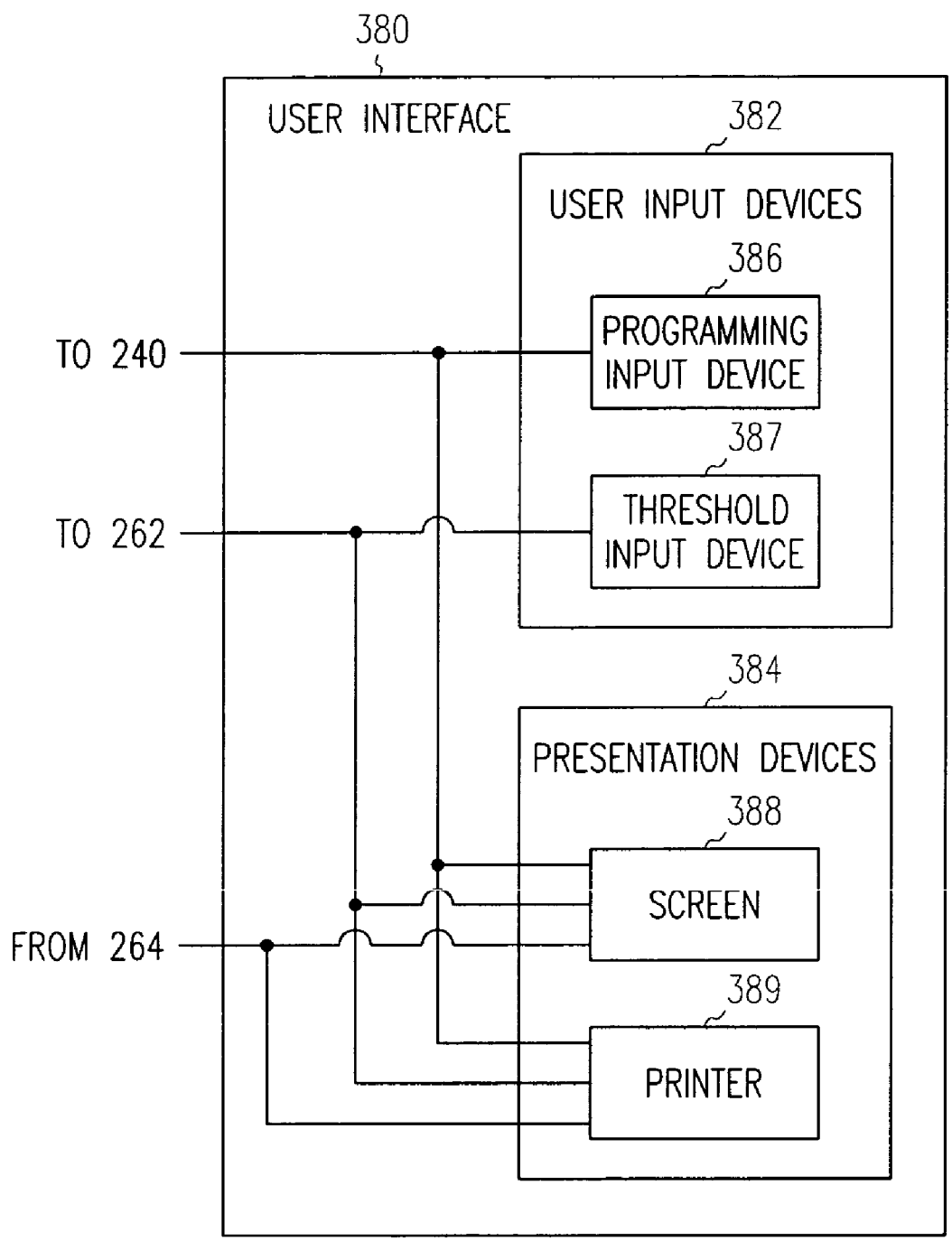
FIG. 3 is a block diagram illustrating an embodiment of a user interface of the CRM system.

FIG. 3 is a block diagram illustrating an embodiment of a user interface 380. User interface 380 is a specific embodiment of user interface 280 and includes user input devices 382 and presentation devices 384. User input devices 382 includes a programming input device 386 and a threshold input device 387. Programming input device 386 receives user inputs related to the programming of implantable medical device 210, such as therapy commands and parameters, from the physician or other caregiver and sends the user inputs to programming circuit 240. Threshold input device 387 receives the threshold QRS width from the physician or other caregiver and sends the threshold QRS width to wide-QRS detector 262. In one embodiment, threshold input device 387 allows the physician or other caregiver to type in the threshold QRS width. In another embodiment, threshold input device 387 allows the physician or other caregiver to select from a plurality of predetermined threshold QRS widths. Presentation devices 384 include a screen 388 and a printer 389. In response to a wide-QRS indication produced by wide-QRS indicator 264, an alert message indicating a wide QRS complex is displayed on screen 388 and/or printed by printer 389. In one embodiment, presentation devices 384 further include a speaker to produce an audio tune to attract attention from the physician or other caregiver to the detection of the wide QRS complex.

Figure 4:
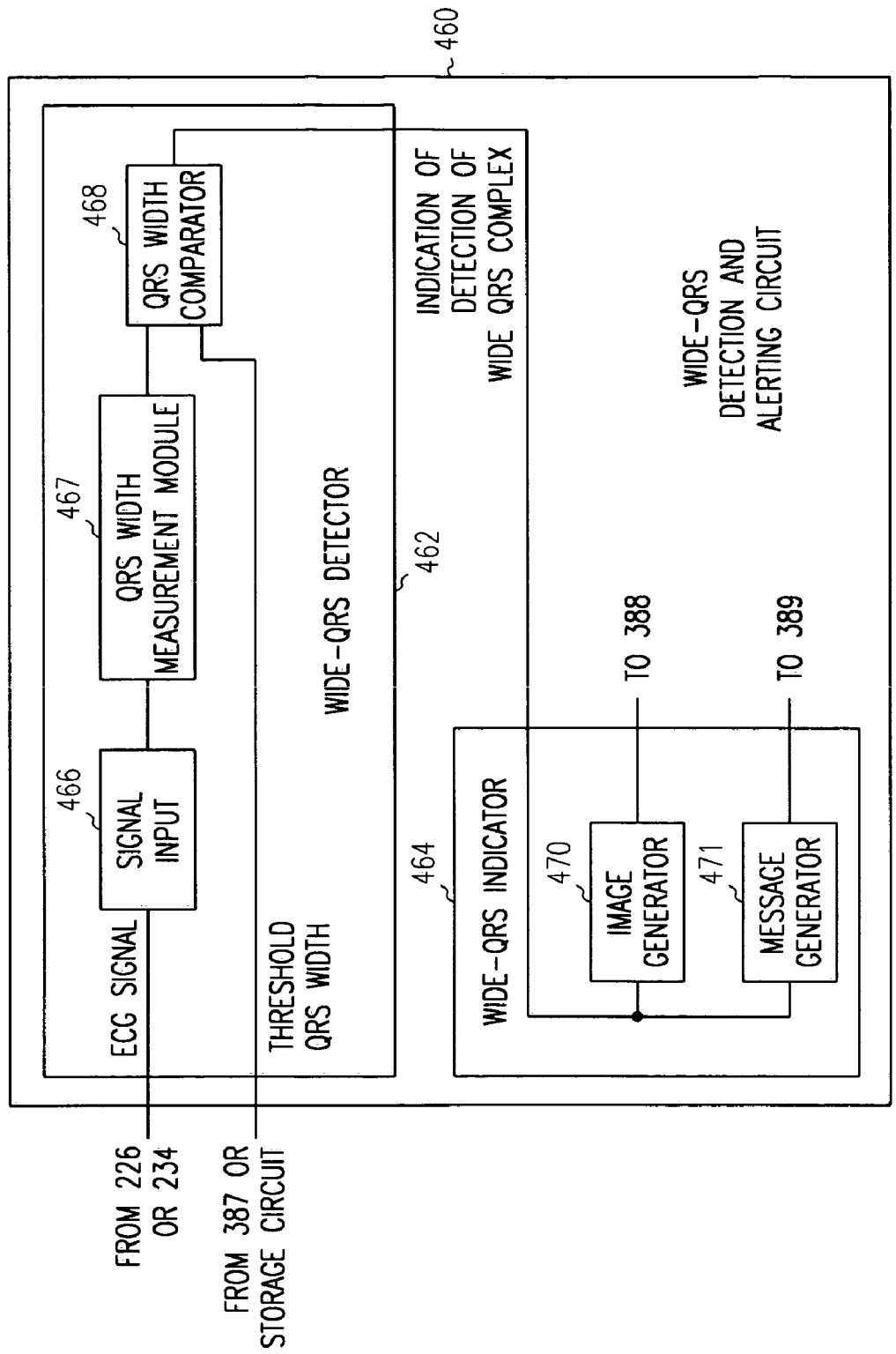
FIG. 4 is a block diagram illustrating an embodiment of a wide-QRS detection and alerting circuit of the CRM system.

FIG. 4 is a block diagram illustrating an embodiment of a wide-QRS detection and alerting circuit 460. Wide-QRS detection and alerting circuit 460 is a specific embodiment of wide-QRS detection and alerting circuit 260 and includes a wide-QRS detector 462 and a wide-QRS indicator 464. In one embodiment, wide-QRS detection and alerting circuit 460 detects wide QRS complexes from a surface ECG signal. In another embodiment, wide-QRS detection and alerting circuit 460 detects wide QRS complexes from a wireless ECG signal. In another embodiment, wide-QRS detection and alerting circuit 460 is selectively programmable for detecting wide QRS complexes from one of a surface ECG and a wireless ECG.

Wide-QRS detector 462 is a specific embodiment of wide-QRS detector 262 and includes a signal input 466, a QRS width measurement module 467, and a QRS width comparator 468. Signal input 466 receives an ECG signal from which wide QRS complexes are to be detected. In one embodiment, signal input 466 receives a surface ECG signal from surface ECG sensing circuit 234. In another embodiment, signal input 466 receives a wireless ECG signal from external telemetry circuit 226. In another embodiment, signal input 466 is programmable for either receiving the surface ECG signal from surface ECG sensing circuit 234 or receiving the wireless ECG signal from external telemetry circuit 226. QRS width measurement module 467 measures the QRS width from the ECG signal received by signal input 466. In one embodiment, QRS width measurement module 467 includes a peak detector and a deviation detector. The peak detector detects R-wave peaks. The deviation detector detects points on the ECG signal where the amplitude deviates from its baseline value. Upon detection of an R-wave peak, QRS width measurement module 467 measures the time interval between two adjacent deviation points detected before and after the R-wave peak. This time interval is the QRS width. In one embodiment, to measure a QRS width, the peak detector detects an R-wave peak, and the deviation detector detects the deviation points by assessing a series of digitized points of the ECG signal before and after the R-wave peak to determine when the ECG signal deviates from the baseline by a predetermined percentage, such as approximately 10%. The deviation points include two points, one before the R-wave peak and one after the R-wave peak, that are the points closest to the R-wave peak and where the ECG signal deviates from the baseline by the predetermined percentage. In one specific embodiment, the percentage is programmable. The QRS width equals the sampling rate multiplied by the number of the digitized points (samples) between the two deviation points. In a further embodiment, QRS width measurement module 467 measures the QRS width when the R-wave peaks are detected at a rate between approximately 30 beats per minute to 300 beats per minute, which corresponding to a rate interval of 200 milliseconds to 2 seconds. QRS width comparator 468 has a first input, a second input, and an output. The first input of QRS width comparator 468 receives the QRS width from QRS width measurement module 467. The second input of QRS width comparator 468 receives a predetermined threshold QRS width. In one embodiment, the second input receives a predetermined threshold QRS width from threshold input device 387. In another embodiment, the predetermined threshold QRS width is a built-in or default value stored in a storage circuit of external system 230. In one embodiment, the built-in or default values is used unless and until the physician or caregiver changes it using threshold input device 387. In one embodiment, the built-in or default value is about 120 milliseconds. The output of QRS width comparator 468 indicates a detection of the wide QRS complex when the QRS width exceeds the predetermined threshold QRS width.

Wide-QRS indicator 464 is a specific embodiment of wide-QRS indicator 264 and includes an image generator 470 and a message generator 471. Image generator 470 produces a visual indication of the detection of the wide QRS complex to present on screen 388. In one embodiment, upon detection of the wide QRS complex, image generator 470 causes a message window to pop up on screen 388. The window displays a conspicuous message such as "Wide QRS Complex" or "Attention: Wide QRS." In a further embodiment, image generator 470 also causes the measured QRS width to be displayed in the message window. Message generator 471 produces a message indicative of the detection of the wide QRS complex to print by printer 389. In one embodiment, the message includes a conspicuously printed header such as "Wide QRS Complex" or "Attention: Wide QRS" followed by the measured QRS width.

In one embodiment, external system 230 includes a medical device programmer. In a specific embodiment, the medical device programmer detects the wide QRS complex from the surface ECG signal. The implantable medical device communicating with the medical device programmer does not necessarily sense a wireless ECG. In another specific embodiment, the medical device programmer detects the wide QRS complex from the wireless ECG signal. When the medical device programmer communicates with an implantable medical device that senses a wireless ECG, there is no need to attach surface ECG electrodes and connecting the surface ECG electrodes to the medical device programmer using an ECG lead cable. In another specific embodiment, as illustrated in FIG. 2, the medical device programmer is capable of detecting QRS width from either the surface ECG signal or the wireless ECG signal. One of the surface ECG signal and the wireless ECG signal is selected for detecting wide QRS complexes based on whether the wireless ECG signal is available and/or the quality of each available ECG signal.

Figure 5:
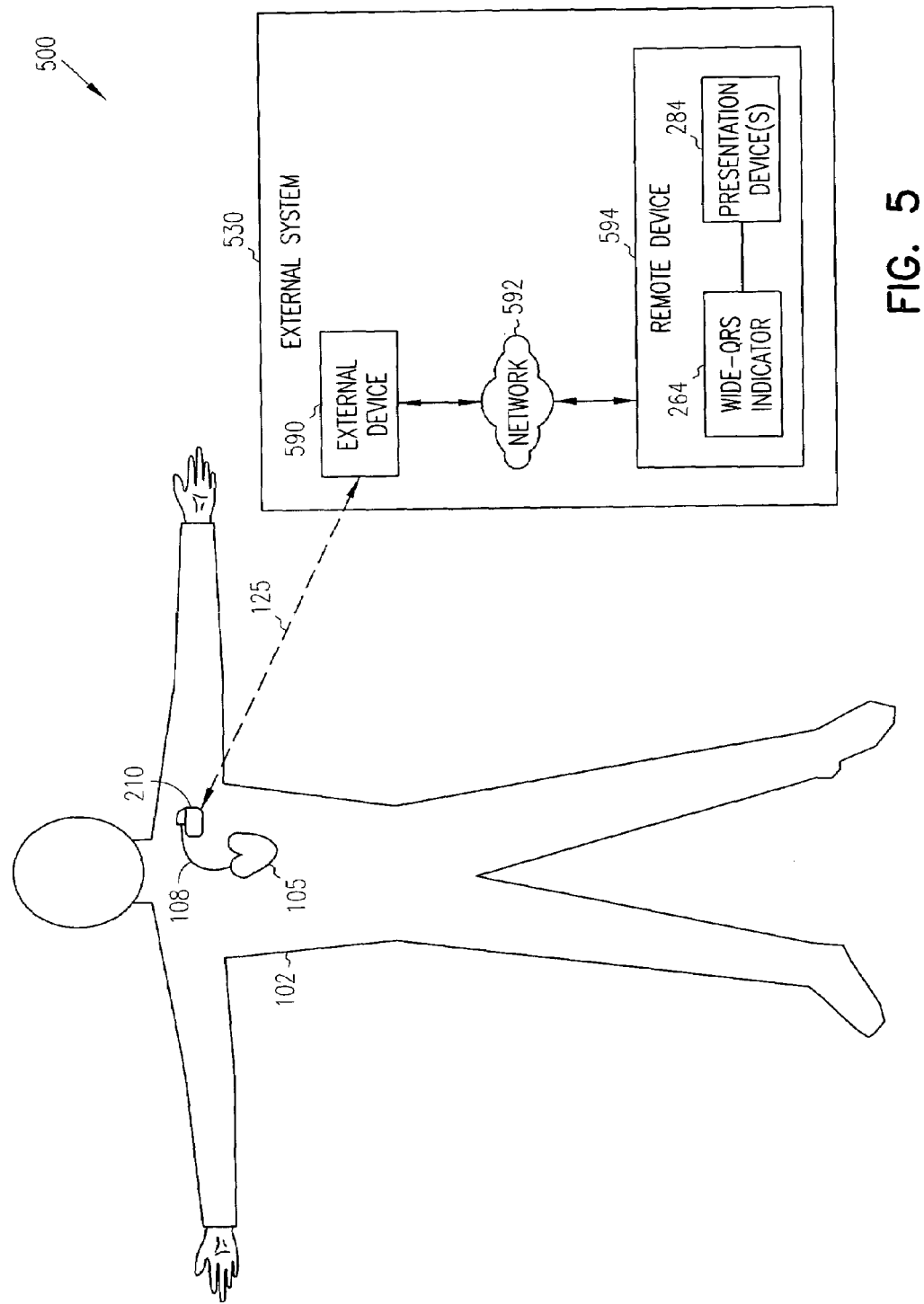
FIG. 5 is an illustration of an embodiment of the CRM system including an external patient management system and portions of the environment in which the CRM system is used.

In another embodiment, external system 230 is a patient monitoring system that is illustrated in FIG. 5 as external system 530. FIG. 5 is an illustration of an embodiment of a CRM system 500 and portions of an environment in which CRM system 500 is used. CRM system 500 is a specific embodiment of CRM system 100. External system 530 includes an external device 590, a remote device 594, and a telecommunication network 592 coupled between external device 590 and remote device 594. In one embodiment, external system 530 includes the elements of external 230 as illustrated in FIG. 2 except for surface ECG sensing circuit. The distribution of the elements in external system 530 depends on design and patient management considerations. In one exemplary embodiment, external device 590 includes at least external telemetry circuit 226 to receive the wireless ECG signal from implantable medical device 210. Remote device 594 includes at least wide-QRS indicator 264 and presentation device(s) 284. Upon detection of the wide QRS complex, remote device 592 informs the physician or other caregiver in a location remote from the patient. This allows prompt medical attention, for example, when the patient's cardiac condition worsens. In one embodiment, upon detection of the wide QRS complex, external system 530 programs implantable medical device 210 to adjust a therapy, such as to start delivering pacing pulses by executing the CRT algorithm.

Figure 6:
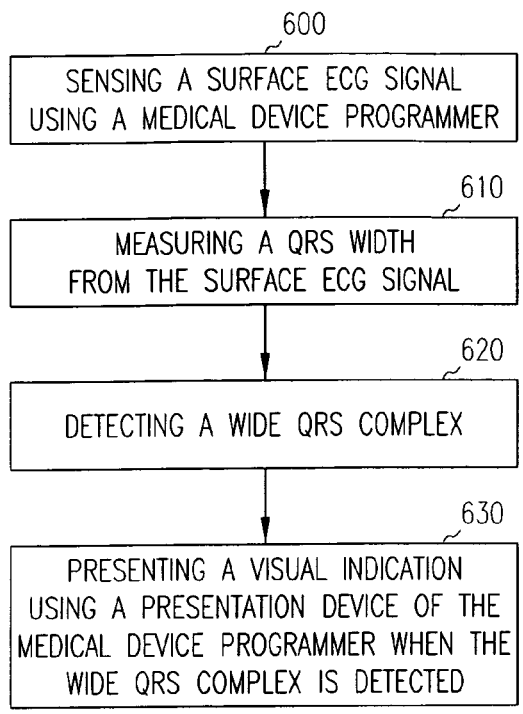
FIG. 6 is a flow chart illustrating one embodiment of a method for detecting and indicating wide QRS complexes using a medical device programmer.

FIG. 6 is a flow chart illustrating one embodiment of a method for detecting and indicating wide QRS complexes using a medical device programmer communicating with an implantable medical device. A surface ECG is sensed, at 600, using a surface ECG sensing circuit of the medical device programmer. A QRS width is measured from the surface ECG signal at 610. A wide QRS complex is detected by comparing the QRS width to a predetermined threshold QRS width at 620. When the QRS width exceeds the predetermined threshold QRS width, a visual indication of a detection of the wide QRS complex is presented, at 630, using a presentation device of the medical device programmer. In one embodiment, the visual indication of the detection of the wide QRS complex is presented on a display screen of the medical device programmer. In another embodiment, a message indicative of the detection of the wide QRS complex is printed using a printer of the medical device programmer.

In one embodiment, the predetermined threshold QRS width is stored in the medical device programmer. In a further embodiment, the store threshold QRS threshold is a default value that is changed when another threshold QRS width is received through a user input device of the medical device programmer.

In one embodiment, the implantable medical device is programmed to adjust a therapy delivery, and the QRS width is measured after the therapy delivery is adjusted. For example, to detect wide QRS complexes based on intrinsic (non-paced) QRS widths of a patient receiving a pacing therapy, the physician or other caregiver programs the implantable medical device to stop the delivery of the pacing therapy using the medical device programmer. To evaluate the effect of pacing or one or more pacing parameters in the QRS width, the physician or other caregiver programs the implantable medical device to start the delivery of the pacing therapy and/or to adjust one or more pacing parameters using the medical device programmer.

Figure 7:
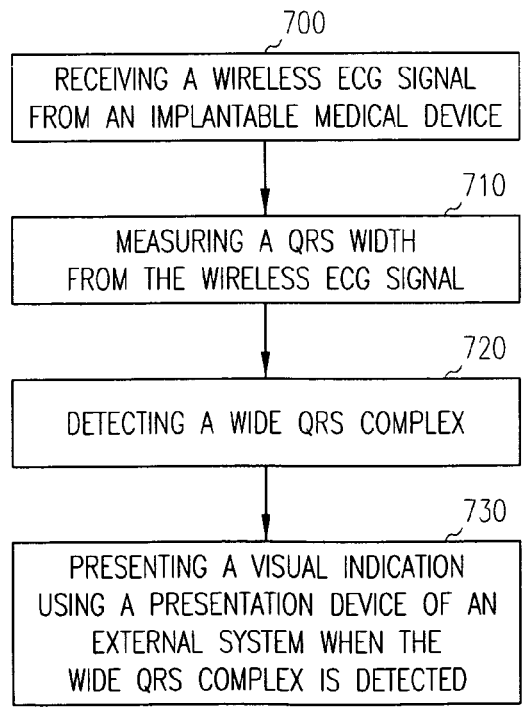
FIG. 7 is a flow chart illustrating one embodiment of a method for detecting and indicating wide QRS complexes based on a wireless ECG signal sensed by an implantable medical device.

FIG. 7 is a flow chart illustrating one embodiment of a method for detecting and indicating wide QRS complexes based on a wireless ECG signal sensed by an implantable medical device. The wireless ECG signal is received from the implantable medical device at 700. In one embodiment, the wireless ECG is a subcutaneous ECG signal sensed through subcutaneous electrodes attached to the implantable medical device. A QRS width is measured from the wireless ECG signal at 710. A wide QRS complex is detected, at 720, by comparing the QRS width to a predetermined threshold QRS width. When the QRS width exceeds the predetermined threshold QRS width, a visual indication of a detection of the wide QRS complex is presented, at 730, using a presentation device of an external system communicating with the implantable medical device. In one embodiment, the visual indication of the detection of the wide QRS complex is presented on a display screen of the external system. In another embodiment, a message indicative of the detection of the wide QRS complex is presented using a printer of the external system.

In one embodiment, the predetermined threshold QRS width is pre-stored. In a further embodiment, the pre-stored threshold QRS threshold is a default value that is changed when another threshold QRS width is entered by the physician or other caregiver.

In one embodiment, the detection of the wide QRS complex is indicated to the physician or other caregiver at a location remote from the patient. The physician or other caregiver determines the need to start, stop, or adjust a therapy delivery, such as based on additional information acquired by the implantable medical device and transmitted to the remote location through the external system. In a further embodiment, the external system starts, stops, or adjusts a therapy delivery based on the information received from the implantable medical device. In one embodiment, in response to the detection of the wide QRS complex, the implantable medical device is programmed to adjust therapy parameters.

It is to be understood that the above detailed description is intended to be illustrative, and not restrictive. Other embodiments, including any possible permutation of the system components discussed in this document, will be apparent to those of skill in the art upon reading and understanding the above description. The scope of the invention should, therefore, be determined with reference to the appended claims, along with the full scope of equivalents to which such claims are entitled.

What is claimed is:

1. A cardiac rhythm management (CRM) system, comprising:
   an implantable medical device including:
      a pacing circuit to deliver pacing pulses; and
      an implant controller, coupled to the pacing circuit, to control the delivery of the pacing pulses; and
   an external system communicatively coupled to the implantable medical device via telemetry, the external system including:
      a user interface including one or more user input devices and one or more presentation devices;
      a programming circuit, coupled to the user interface, to program the implantable medical device; and
      a wide-QRS detection and alerting circuit coupled to the user interface, the wide-QRS detection and alerting circuit including:
         a wide-QRS detector to receive an electrocardiogram (ECG) signal and detect a wide QRS complex from the ECG signal; and
         a wide-QRS indicator, coupled to the wide-QRS detector, to produce a wide-QRS indication including text directly indicating the detection of the wide QRS complex using the one or more presentation devices in response to the detection of the wide QRS complex.

2. The CRM system of claim 1, wherein the implant controller comprises a cardiac resynchronization therapy (CRT) algorithm execution module to control a delivery of pacing pulses by executing a CRT algorithm.

3. The CRM system of claim 1, wherein the one or more presentation devices comprise a screen, and the wide-QRS indicator comprises an image generator to produce a visual indication of the detection of the wide QRS complex to present on the screen.

4. The CRM system of claim 1, wherein the one or more presentation devices further comprise a printer, and the wide-QRS indicator comprises a message generator to produce a message indicative of the detection of the wide QRS complex to print using the printer.

5. The CRM system of claim 1, wherein the external system comprises a medical device programmer including the user interface, the programming circuit, and the wide-QRS detection and alerting circuit.

6. The CRM system of claim 5, wherein the ECG signal comprises a surface ECG signal, wherein the medical device programmer comprises a surface ECG sensing circuit to sense the surface ECG signal, and wherein the wide-QRS detector is adapted to receive the surface ECG signal and detect the wide QRS complex from the surface ECG signal.

7. The CRM system of claim 1, further comprising a plurality of implantable ECG electrodes, and wherein the implantable medical device comprises a wireless ECG sensing circuit, coupled to the implantable ECG electrodes, to sense a wireless ECG signal being a signal sensed through the plurality of implantable electrodes and approximating a surface ECG signal, and wherein the wide-QRS detector is adapted to receive the wireless ECG signal and detect the wide QRS complex from the wireless ECG signal.

8. The CRM system of claim 7, wherein the plurality of implantable ECG electrodes comprise a plurality of implantable subcutaneous electrodes.

9. A medical device programmer for communicating with an implantable medical device, the medical device programmer comprising:
   an external telemetry circuit to communicate with the implantable medical device;
   a user interface including one or more user input devices and one or more presentation devices;
   a programming circuit, coupled to the user interface an the external telemetry circuit, to program the implantable medical device;
   a surface electrocardiogram (ECG) sensing circuit to sense at least one surface ECG signal; and
   a wide-QRS detection and alerting circuit coupled to the use interface, the wide-QRS detection and alerting circuit including:
      a wide-QRS detector, coupled to the surface ECG sensing circuit, to receive the at least one surface ECG signal and detect a wide QRS complex from the at least one surface ECG signal; and
      a wide-QRS indicator coupled to the wide-QRS detector, the wide-QRS indicator adapted to receive an indication of detection of the QRS complex and produce a wide-QRS indication including text directly indicating the detection of the wide QRS complex using the one or more presentation devices when the detection of the wide QRS complex is indicated.

10. The medical device programmer of claim 9, wherein the wide-QRS detector comprises:
    a signal input, coupled to the surface ECG sensing circuit, to receive the at least one surface ECG signal;
    a QRS width measurement module, coupled to the signal input, to measure a QRS width from the at least one surface ECG signal;
    a QRS width comparator including a first input to receive the QRS width, a second input to receive a predetermined threshold QRS width and an output indicative of a detection of a wide QRS complex when the QRS width exceeds the predetermined threshold QRS width.

11. The medical device programmer of claim 10, wherein the one or more user input device comprise a threshold input device to receive the predetermined threshold QRS width.

12. The medical device programmer of claim 9, wherein the one or more presentation devices comprise a screen, and the wide-QRS indicator comprises an image generator to produce a visual indication of the detection of the wide QRS complex to present on the screen.

13. The medical device programmer of claim 12, wherein the one or more presentation devices further comprise a printer, and the wide-QRS indicator comprises a message generator to produce a message indicative of the detection of the wide QRS complex to print using the printer.

14. The medical device programmer of claim 13, wherein the one or more user input device comprise a programming input device receiving at least pacing parameters for programming the implantable medical device.

15. An external system for communicating with an implantable medical device coupled to implantable electrodes, the external system comprising;
    an external telemetry circuit to receive at least one wireless electrocardiogram (ECG) signal from the implantable medical device, the wireless ECG signal being a signal sensed through the implantable electrodes and approximating a surface ECG signal;

a programming circuit, coupled to the external telemetry circuit, to program the implantable medical device;

a user interface including one or more presentation devices; and a wide-QRS detection and alerting circuit coupled to the external telemetry circuit and the user interface, the wide-QRS detection and alerting circuit including:

a wide-QRS detector to receive the at least one wireless ECG signal and detect a wide QRS complex from the at least one wireless ECG signal; and a wide-QRS indicator coupled to the wide-QRS detector, the wide-QRS detector adapted to produce a wide-QRS indication including text directly indicating the detection of the wide QRS complex using the one or more presentation devices, the wide-QRS indication being an indication of a detection of the wide QRS complex.

16. The external system of claim 15, wherein the wide-QRS detector comprises:

a signal input, coupled to the external telemetry circuit, to receive the at least one wireless ECG signal;

a QRS width measurement module, coupled to the signal input, to measure a QRS width from the at least one wireless ECG signal; and a QRS width comparator including a first input to receive the QRS width, a second input to receive a predetermined threshold QRS width, and an output indicative of a detection of a wide QRS complex when the QRS width exceeds the predetermined threshold QRS width.

17. The external system of claim 16, wherein the user interface comprises a threshold input device to receive the predetermined threshold QRS width.

18. The external system of claim 17, wherein the user interface further comprises a programming input device receiving commands and therapy parameters for programming the implantable medical device.

19. The external system of claim 17, wherein the one or more presentation devices comprise a screen, and the wide-QRS indicator comprises an image generator to produce a visual indication of the detection of the wide QRS complex to present on the screen.

20. The external system of claim 17, wherein the one or more presentation devices further comprise a printer, and the wide-QRS indicator comprises a message generator to produce a message indicative of the detection of the wide QRS complex to print using the printer.

21. The external system of claim 20, comprising an external device communicatively coupled to the implantable medical device via the telemetry, a remote device, and a telecommunication network coupled between the external device and the remote device.

22. The external system of claim 21, wherein the remote device comprises at least one of the one or more presentation devices.

23. A method for operating a medical device programmer communicating with an implantable medical device, the method comprising:

sensing a surface electrocardiogram (ECG) signal using a surface ECG sensing circuit of the medical device programmer;

measuring a QRS width from the surface ECG signal;

detecting a wide QRS complex by comparing the measured QRS width to a predetermined threshold QRS width; and presenting a visual indication including text directly indicating a detection of the wide QRS complex using a presentation device of the medical device programmer in response to the detection of the wide QRS complex.

24. The method of claim 23, wherein presenting the visual indication comprises presenting the visual indication of the detection of the wide QRS complex on a display screen of the medical device programmer.

25. The method of claim 23, wherein presenting the visual indication comprises printing a message indicative of the detection of the wide QRS complex using a printer of the medical device programmer.

26. The method of claim 23, further comprising receiving the predetermined threshold QRS width through a user input device of the external system.

27. The method of claim 26, further comprising programming the implantable medical device using the medical device programmer before measuring the QRS width.

28. The method of claim 27, wherein programming the implantable medical device comprises programming the implantable medical device to start delivering pacing pulses.

29. The method of claim 27, wherein programming the implantable medical device comprises programming the implantable medical device to stop delivering pacing pulses.

30. The method of claim 27, wherein programming the implantable medical device comprises programming the implantable medical device to adjust one or more pacing parameters.

31. A method for operating an external system communicating with an implantable medical device coupled to implantable electrodes, the method comprising:

receiving a wireless electrocardiogram (ECG) signal from the implantable medical device, the wireless ECG signal being a signal sensed through the implantable electrodes and approximating a surface ECG signal;

measuring a QRS width from the wireless ECG signal;

detecting a wide QRS complex by comparing the QRS width to a predetermined threshold QRS width; and presenting a visual indication of a detection of the wide QRS complex including text directly indicating the detection of wide QRS complex using a presentation device of the external system in response to the detection of the wide QRS complex.

32. The method of claim 31, wherein presenting the visual indication of the detection of the wide QRS complex comprises presenting the visual indication of the detection of the wide QRS complex on a display screen of the external system.

33. The method of claim 31, wherein presenting the visual indication of the detection of the wide QRS complex comprises printing a message indicative of the detection of the wide QRS complex using a printer of the external system.

34. The method of claim 31, further comprising receiving the predetermined threshold QRS width through a user input device of the external system.

35. The method of claim 34, further comprising programming the implantable medical device to adjust a delivery of pacing pulses in response to the detection of the wide QRS complex.

* * * * *

UNITED STATES PATENT AND TRADEMARK OFFICE
CERTIFICATE OF CORRECTION

PATENT NO. : 7,283,864 B2  Page 1 of 1
APPLICATION NO. : 11/055731
DATED : October 16, 2007
INVENTOR(S) : Thomas et al.

It is certified that error appears in the above-identified patent and that said Letters Patent is hereby corrected as shown below:

In column 12, line 11, in Claim 9, delete "an" and insert -- and --, therefor.

In column 12, line 17, in Claim 9, delete "use" and insert -- user --, therefor.

Signed and Sealed this

Twenty-sixth Day of February, 2008

JON W. DUDAS
*Director of the United States Patent and Trademark Office*